(12) United States Patent
Kurosu et al.

(10) Patent No.: US 8,460,485 B2
(45) Date of Patent: Jun. 11, 2013

(54) METHOD OF FORMING FINE GRAINS OF CO-CR-MO ALLOY WITH NITROGEN ADDITION AND CO-CR-MO ALLOY WITH NITROGEN ADDITION

(75) Inventors: Shingo Kurosu, Sendai (JP); Akihiko Chiba, Saendai (JP); Hiroaki Matsumoto, Sendai (JP)

(73) Assignee: Tohoku University, Sendai (JP)

( * ) Notice: Subject to any disclaimer, the term of this patent is extended or adjusted under 35 U.S.C. 154(b) by 0 days.

(21) Appl. No.: 13/060,593

(22) PCT Filed: Sep. 2, 2009

(86) PCT No.: PCT/JP2009/065358
§ 371 (c)(1),
(2), (4) Date: Feb. 24, 2011

(87) PCT Pub. No.: WO2010/026996
PCT Pub. Date: Mar. 11, 2010

(65) Prior Publication Data
US 2011/0209799 A1 Sep. 1, 2011

(30) Foreign Application Priority Data
Sep. 5, 2008 (JP) ................................. 2008-227875

(51) Int. Cl.
*C22F 1/10* (2006.01)
(52) U.S. Cl.
USPC .......................................... 148/674; 148/425

(58) Field of Classification Search
USPC ................................................. 148/425, 674
See application file for complete search history.

(56) References Cited

U.S. PATENT DOCUMENTS 4,116,724 A 9/1978 Hirschfeld et al.
2004/0236433 A1 11/2004 Kennedy et al.

FOREIGN PATENT DOCUMENTS

| JP | A-52-139619 | 11/1977 |
| JP | A-2002-363675 | 12/2002 |
| JP | A-2006-265633 | 10/2006 |
| JP | A-2007-502372 | 2/2007 |
| JP | A-2008-111177 | 5/2008 |

OTHER PUBLICATIONS

International Search Report dated Dec. 1, 2009 in corresponding International Application No. PCT/JP2009/065358 (with translation).

*Primary Examiner* — Steven Bos
*Assistant Examiner* — Brian Walck
(74) *Attorney, Agent, or Firm* — Oliff & Berridge, PLC

(57) ABSTRACT

A Co—Cr—Mo alloy with nitrogen addition composed of 26 to 35% by weight of Cr, 2 to 8% by weight of Mo, 0.1 to 0.3% by weight of N, and balance of Co is subjected to solution treatment and then subjected to isothermal aging treatment holding the alloy at 670 to 830° C. for a predetermined period of time to form a multi-phase structure composed of an ε-phase and a Cr nitride by means of an isothermal aging effect. After cooling, the alloy subjected to reverse transformation treatment in which the alloy is heated at a temperature range of 870 to 1100° C. for reverse transformation to a single γ-phase from the multi-phase structure composed of an ε-phase and a Cr nitride.

7 Claims, 5 Drawing Sheets

METHOD OF FORMING FINE GRAINS OF CO-CR-MO ALLOY WITH NITROGEN ADDITION AND CO-CR-MO ALLOY WITH NITROGEN ADDITION

TECHNICAL FIELD

The present invention relates to a method of forming fine grains of a Co—Cr—Mo alloy with nitrogen addition, which is widely used as an artificial knee or hip joint implant material or as a dental implant material, and relates to a Co—Cr—Mo alloy with nitrogen addition produced by the method.

BACKGROUND ART

Co—Cr—Mo alloys are excellent in mechanical properties, wear resistance, and corrosion resistance and are therefore widely used as artificial knee or hip joint implant materials or as dental implant materials. Products thereof are mainly produced by molding through casting. The structure of a typical Co—Cr—Mo ASTM standard F75 alloy is constituted of a dendrite structure mainly composed of a Co-rich γ (FCC) phase, a Cr-rich $M_{23}C_6$ carbide phase containing Co and Mo, and a Cr- and Mo-rich σ-phase. This casting material contains many casting defects such as hard brittle precipitation, segregation, shrinkage cavities, and pin hole, and these defects cause fracture and cracking during thermomechanical treatment to deteriorate mechanical reliability.

Accordingly, heat treatment for homogenization is performed for improving the toughness and the elongation property, but disappearance of deposition due to the heat treatment causes coarsening of the casting material, which may deteriorate yield strength and fatigue strength. In order to solve this problem, hot forging that can adjust thermal history of the casting material is usually performed. The hot forging collapses the internal defects contained in the casting material and also destroys the dendrite structure to improve the mechanical reliability. In addition, a fine structure can be formed by the dynamic recrystallization that occurs during the hot forging (for example, see JP-A-2002-363675).

Furthermore, the hard brittle σ-phase, which hinders plastic workability, is eliminated by adding nitrogen to the Co—Cr—Mo alloy. As a result, a Co-base alloy having a crystal structure in which the phase ratio of the γ-phase is 80% or more as the volume ratio, which can be applied to a living body, can be produced. Thus, an alloy excellent in plastic workability can be obtained (for example, see JP-A-2008-111177). In also such a case, in order to refine the crystal grains and to increase plastic workability, it is necessary to perform hot forging.

CITATION LIST

Patent Literature

Patent Literature 1: JP-A-2002-363675
Patent Literature 2: JP-A-2008-111177

SUMMARY OF INVENTION

Technical Problem

However, in the methods described in JP-A-2002-363675 and JP-A-2008-111177, if the plastic strain introduced in the hot forging is heterogeneous, there is a problem of difficulty in making a uniform fine grain in the entire cross section of a forged product. For example, as shown in FIG. 10, in a case that a round bar material is produced by hot swage, if the plastic strain introduced in the forging differs at the portion near the surface and at the central portion, it can be confirmed that the grain diameter at the portion near the surface of the produced round bar material is different from that at the central portion. In hot forging of a Co—Cr—Mo alloy, it is necessary to understand the detailed temperature profiles of a workpiece. Thus, there is a problem that a high degree of specialization is required in those who conduct the hot forging.

The present invention has been made in the view of the above problems, and it is an object of the present invention to provide a method of forming fine grains of a Co—Cr—Mo alloy with nitrogen addition in which uniform fine grain structure can be easily obtained only by heat treatment, without performing thermomechanical treatment, such as hot forging, utilizing recrystallization and to provide a Co—Cr—Mo alloy with nitrogen addition.

Solution to Problem

In order to achieve the above-mentioned object, the method of forming fine grains of a Co—Cr—Mo alloy with nitrogen addition according to the present invention includes subjecting a Co—Cr—Mo alloy with nitrogen addition composed of 26 to 35% by weight of Cr, 2 to 8% by weight of Mo, 0.1 to 0.3% by weight of N, and balance of Co to solution treatment; then subjecting the alloy to isothermal aging treatment holding the alloy at 670 to 830° C. for a predetermined period of time to form a multi-phase structure composed of an ε-phase and a Cr nitride by means of an isothermal aging treatment; and, after cooling, subjecting the alloy to reverse transformation treatment in which the alloy is heated at a temperature range of 870 to 1100° C. for reverse transformation to a single γ-phase from the multi-phase structure composed of an ε-phase and a Cr nitride.

The method of forming fine grains of a Co—Cr—Mo alloy with nitrogen addition according to the present invention can easily provide a uniform fine grain structure, without performing thermomechanical treatment, only by heat treatment utilizing reverse transformation, unlike a method forming fine grains by hot forging utilizing recrystallization. The mechanical reliability of the Co—Cr—Mo alloy with nitrogen addition is improved by this formation of fine grains. In addition, since the formation can be performed only by heat treatment, a uniform fine grain can be obtained even if a person who conducts the formation does not have a high degree of specialization.

In the method of forming fine grains of a Co—Cr—Mo alloy with nitrogen addition according to the present invention, since thermomechanical treatment is not necessary, the material to be used may have any shape and size, and even a compact material, a material having a complex shape, or a commercially available product can be formed into fine grains. In addition, since the method does not need a large-sized forging apparatus and does not require a person who conducts the method to have a forging skill, the method is excellent in universal use. The method of forming fine grains of a Co—Cr—Mo alloy with nitrogen addition according to the present invention can be applied to any Co—Cr—Mo alloy with nitrogen addition that forms a multi-phase structure composed of an ε-phase and a Cr nitride by isothermal aging treatment, whatever the process of producing the alloy. Thus, the method can be widely applied. The method of forming fine grains of a Co—Cr—Mo alloy with nitrogen addition according to the present invention may contain other phases up to about 5% as long as reverse transformation to a single γ-phase can be substantially achieved by reverse transformation.

Since reverse transformation treatment at a temperature higher than 1100° C. causes significant coarsening of crystal grains in accordance with elapse of holding time, in order to obtain a fine grain structure, the reverse transformation treatment of the method of forming fine grains of a Co—Cr—Mo alloy with nitrogen addition according to the present invention must be performed at a temperature of 1100° C. or less. In the method of forming fine grains of a Co—Cr—Mo alloy with nitrogen addition according to the present invention, quenching is preferably performed after isothermal aging treatment and also after reverse transformation treatment.

In the method of forming fine grains of a Co—Cr—Mo alloy with nitrogen addition according to the present invention, the Co—Cr—Mo alloy with nitrogen addition that is subjected to solution treatment may contain 0.2% by weight or less of Ni or may contain 0.35% by weight or less of C.

In the method of forming fine grains of a Co—Cr—Mo alloy with nitrogen addition according to the present invention, the holding time for the isothermal aging treatment is preferably 63000 seconds or more. By doing so, a multi-phase structure composed of an s-phase and a Cr nitride can be formed by means of the isothermal aging effect in the entire structure of the alloy.

In the method of forming fine grains of a Co—Cr—Mo alloy with nitrogen addition according to the present invention, the reverse transformation treatment is preferably performed by holding the alloy at a temperature range of 920 to 1000° C. for 300 seconds or more or is preferably performed by holding the alloy at a temperature range of 1000 to 1100° C. for 50 seconds or more. In these cases, the entire alloy structure can be reverse-transformed to a single γ-phase from a multi-phase structure composed of an ε-phase and a Cr nitride.

In the method of forming fine grains of a Co—Cr—Mo alloy with nitrogen addition according to the present invention, after the reverse transformation treatment, the alloy is cooled, and the isothermal aging treatment and the reverse transformation treatment may be further repeated. In such a case, the crystal grains can be further refined. The isothermal aging treatment and the reverse transformation treatment may be repeated one cycle or multiple cycles.

The Co—Cr—Mo alloy with nitrogen addition according to the present invention is produced by the method of forming fine grains of a Co—Cr—Mo alloy with nitrogen addition according to the present invention and is substantially composed of a single γ-phase having an average crystal grain diameter of 25 μm or less.

The Co—Cr—Mo alloy with nitrogen addition according to the present invention can be easily obtained by the method of forming fine grains of a Co—Cr—Mo alloy with nitrogen addition according to the present invention. Since the Co—Cr—Mo alloy with nitrogen addition according to the present invention is substantially composed of a uniform fine grain structure of a γ-phase having an average crystal grain diameter of 25 μm or less, breakage and cracking hardly occur during thermomechanical treatment, and the mechanical reliability is high. The Co—Cr—Mo alloy with nitrogen addition according to the present invention may contain other phases up to about 5% as long as the alloy is substantially a single γ-phase.

According to the present invention, provided is a method of forming fine grains of a Co—Cr—Mo alloy with nitrogen addition in which a uniform fine grain structure can be easily obtained only by heat treatment, without performing thermomechanical treatment such as hot forging utilizing recrystallization, and also provided is a Co—Cr—Mo alloy with nitrogen addition.

DESCRIPTION OF EMBODIMENTS

Preferred embodiments of the present invention will be described below with reference to the drawings.

Figure 1:
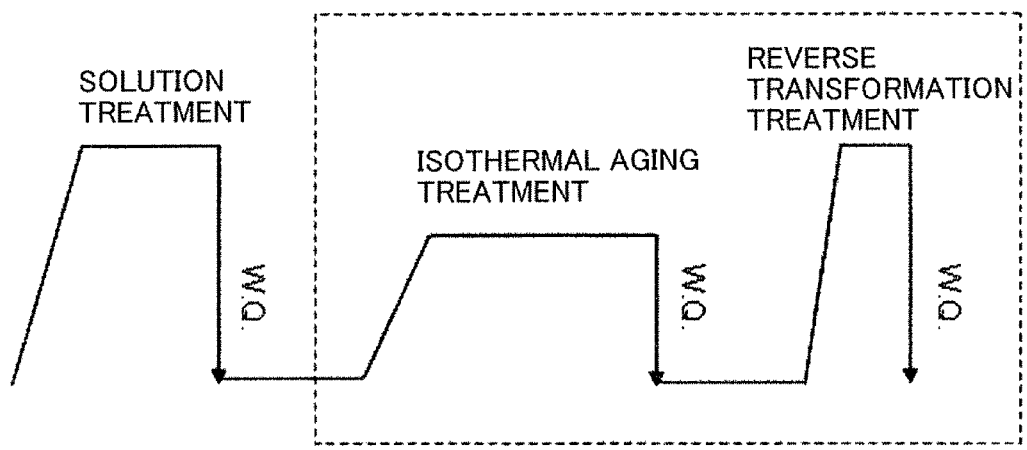
FIG. 1 is a diagram schematically illustrating a heat treatment process of a method of forming fine grains of a Co—Cr—Mo alloy with nitrogen addition according to an embodiment of the present invention.

As shown in FIG. 1, in a method of forming fine grains of a Co—Cr—Mo alloy with nitrogen addition according to an embodiment of the present invention, first, a Co—Cr—Mo alloy with nitrogen addition composed of 26 to 35% by weight of Cr, 2 to 8% by weight of Mo, 0.1 to 0.3% by weight of N, 0 to 0.2% by weight of Ni, 0 to 0.35% by weight of C, and balance of Co is subjected to solution treatment to form a single γ-phase structure and then cooled with water (water quenching: W. Q.). Subsequently, the alloy is held at a temperature of 670 to 830° C. for a predetermined time for isothermal aging treatment to form a multi-phase microstructure composed of an ε-phase and a Cr nitride by means of the isothermal aging treatment and then cooled with water (W. Q.). Then, the alloy is heated at a temperature range of 870 to 1100° C. for reverse transformation treatment of the multi-phase structure composed of an ε-phase and a Cr nitride into a single γ-phase by means of reverse transformation.

Example 1

1. Experimental method

An ingot of a Co—Cr—Mo alloy with nitrogen addition was formed by high-frequency induction melting so that the sample alloy had a composition, as shown in Table 1, composed of 27.5% by weight of Cr, 5.5% by weight of Mo, 0.12% by weight of Ni, 0.04% by weight of C, 0.16% by weight of N, and 66.68% by weight of Co. The nitrogen was added as $Cr_2N$ powder. The material formed by melting was subjected to heat treatment for homogenization, followed by hot forging for destroy the cast structure. The resulting alloy was used as a starting sample to be subjected to each heat treatment.

TABLE 1

| Co | Cr | Mo | Ni | C | N |
|---|---|---|---|---|---|
| Bal. | 27.5 mass % | 5.5 mass % | 0.12 mass % | 0.04 mass % | 0.16 mass % |

2. Solution Treatment

The starting sample was subjected to solution treatment at 1200° C. for 3600 seconds and then cooled with water to form a single γ-phase structure. The average crystal grain diameter at this stage was about 200 μm.

3. Isothermal Aging Treatment

Figure 2:
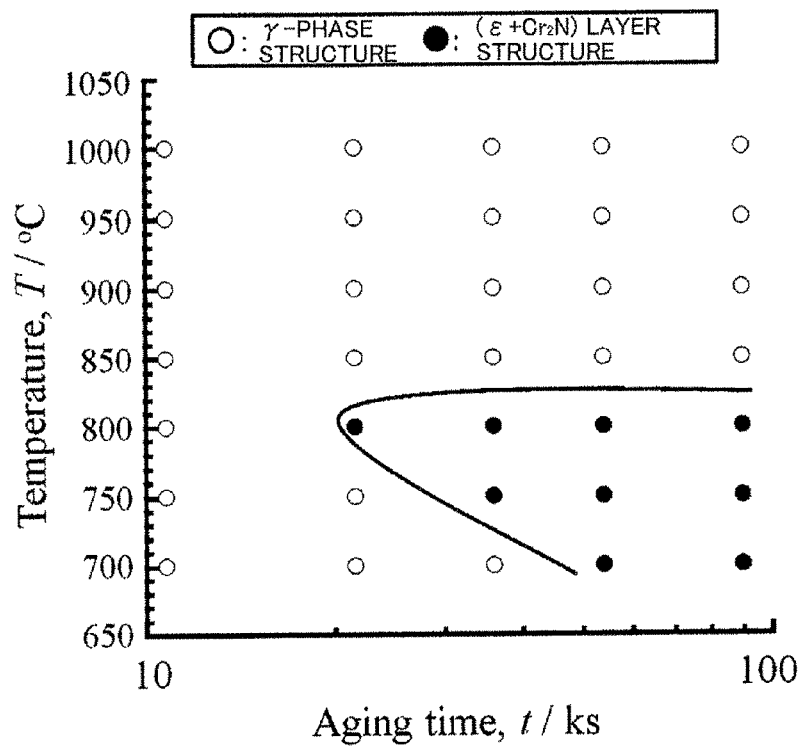
FIG. 2 is a TTT diagram (Time-Temperature-Transformation diagram) of a sample subjected to isothermal aging treatment of the method of forming fine grains of Co—Cr—Mo alloy with nitrogen addition according to an embodiment of the present invention.

Then, each sample after solution treatment was held at various temperatures by 90000 seconds for isothermal aging. FIG. 2 is a time-temperature-transformation (TTT) diagram (Time-Temperature-Transformation diagram) drawn based on structure inspection of the samples subjected to isothermal aging treatment at various temperatures. As shown in FIG. 2, in the Co—Cr—Mo alloy with nitrogen addition, it can be confirmed that the isothermal aging treatment at 700 to 800° C. forms a multi-phase structure composed of an ε-phase and a Cr nitride from the γ-phase. In particular, isothermal aging treatment at 800° C. can firstly form the multi-phase structure and is therefore effective. In order to form the multi-phase structure in the entire structure by the isothermal aging treatment at 800° C., an aging time of 63000 seconds or more is necessary. In isothermal aging treatment at a temperature range of 800° C. or less, since a multi-phase structure is not entirely formed in the structure even in an aging time of 90000 seconds or more, it is suggested that isothermal aging treatment at 800° C. is practically most effective for forming a multi-phase structure.

Figure 3:
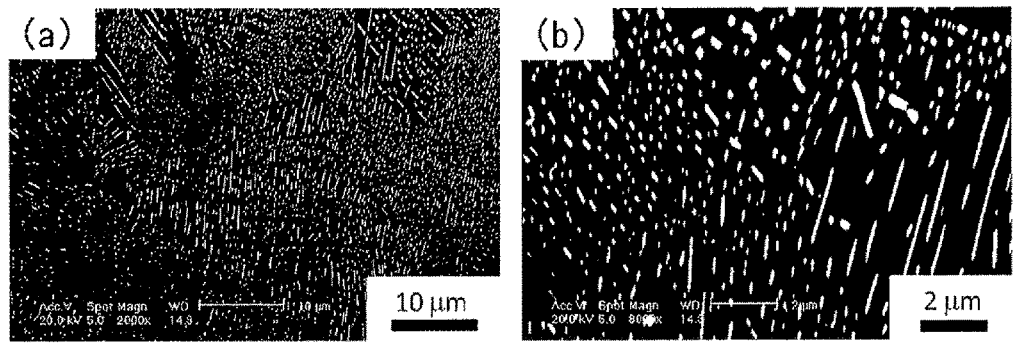
FIG. 3A is a scanning electron micrograph of a multi-phase structure obtained by isothermal aging treatment at 800° C. for 24 hours in the method of forming fine grains of a Co—Cr—Mo alloy with nitrogen addition according to an embodiment of the present invention.
FIG. 3B is a scanning electron micrograph of the multi-phase structure obtained by the isothermal aging treatment at 800° C. for 24 hours in the method of forming fine grains of a Co—Cr—Mo alloy with nitrogen addition according to the embodiment of the present invention.

FIGS. 3A and 3B are scanning electron microscope (SEM) photographs of a multi-phase structure obtained by isothermal aging treatment at 800° C. for 24 hours. As shown in FIGS. 3A and 3B, the structure is constituted of lamellar blocks of approximately 110 μm, and fine Cr nitride (white portions in FIGS. 3A and 3B) of 1 μm or less is distributed in the crystal grains.

4. Reverse Transformation Treatment

Figure 4:
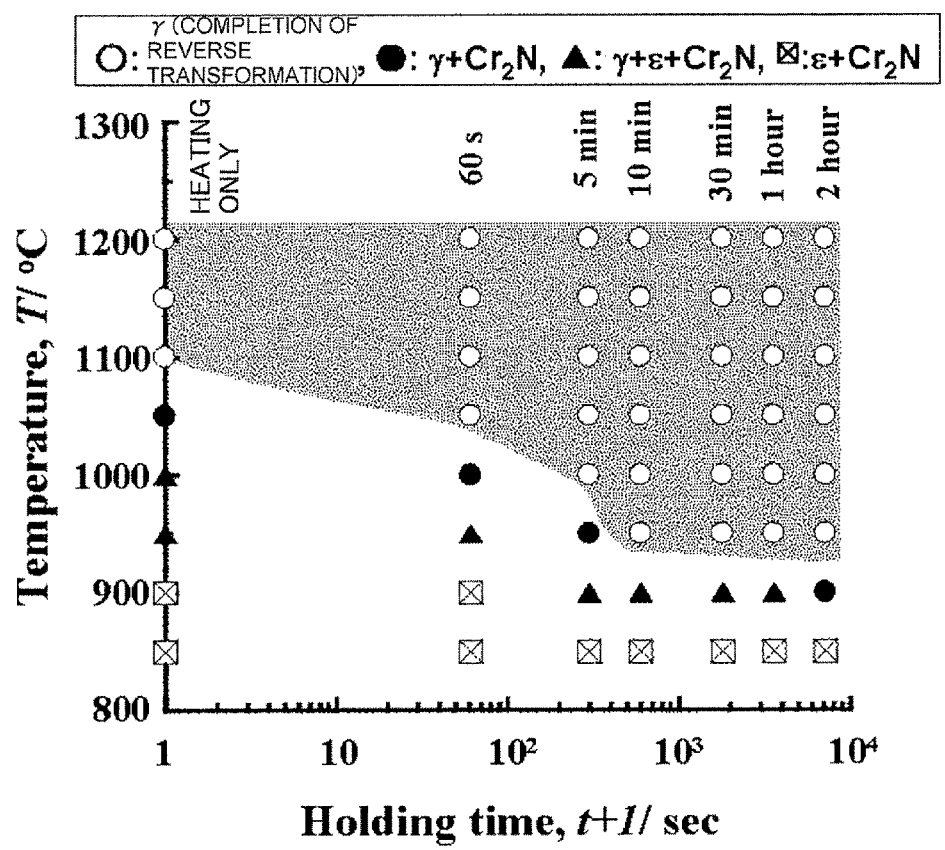
FIG. 4 is a TTT diagram (Time-Temperature-Transformation diagram) of a sample subjected to reverse transformation treatment of the method of forming fine grains of a Co—Cr—Mo alloy with nitrogen addition according to an embodiment of the present invention.

After the isothermal aging treatment at 800° C., the samples were subjected to reverse transformation treatment at a temperature range of 850 to 1200° C., in which the γ-phase is stable, by 7200 seconds (2 hours), and X-ray diffraction and structure inspection of the samples were conducted. The results are shown in FIG. 4. As shown in FIG. 4, the reverse transformation to a single γ-phase from the multi-phase structure composed of an ε-phase and a Cr nitride has been completed in a high temperature range of 950° C. or more and a holding time of 300 seconds or more. In addition, in a high temperature range of 1000° C. or more, the reverse transformation to a single γ-phase from the multi-phase structure composed of an ε-phase and a Cr nitride has been completed in a holding time of 50 seconds or more.

However, since it was confirmed that reverse transformation treatment at a high temperature of 1100° C. or more causes significant coarsening of crystal grains in accordance with elapse of holding time, it is suggested that reverse transformation treatment at a temperature of 1100° C. or less is practically most effective.

Figure 5:
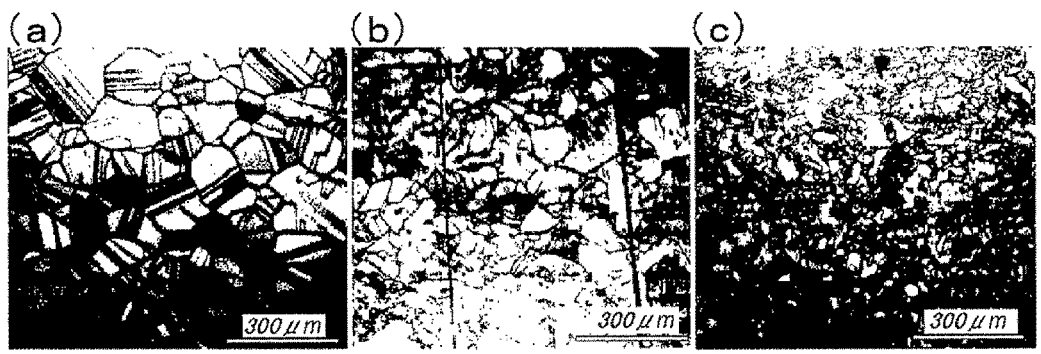
FIG. 5A is an image quality map (IQ map) of an alloy after solution treatment in the method of forming fine grains of a Co—Cr—Mo alloy with nitrogen addition according to an embodiment of the present invention, obtained by an electron back-scatter diffraction pattern (EBSD) technique.
FIG. 5B is an IQ map of the alloy after isothermal aging treatment in the method of forming fine grains of a Co—Cr—Mo alloy with nitrogen addition according to the embodiment, obtained by an EBSD technique.
FIG. 5C is an IQ map of the alloy after reverse transformation treatment in the method of forming fine grains of a Co—Cr—Mo alloy with nitrogen addition according to the embodiment, obtained by an EBSD technique.

FIGS. 5A to 5C are image quality (IQ) maps of an alloy subjected to reverse transformation treatment after isothermal aging treatment, obtained after each treatment by an electron back-scatter diffraction pattern (EBSD) technique. As shown in FIGS. 5A to 5C, the sample subjected to reverse transformation treatment has much more uniform fine grains than the sample after solution treatment and than the sample after isothermal aging treatment. For example, the average crystal grain diameter of a sample subjected to reverse transformation treatment at 1000° C. for 600 seconds was about 20 μm, that is, reduced to one-tenth that of a sample after solution treatment.

Figure 6:
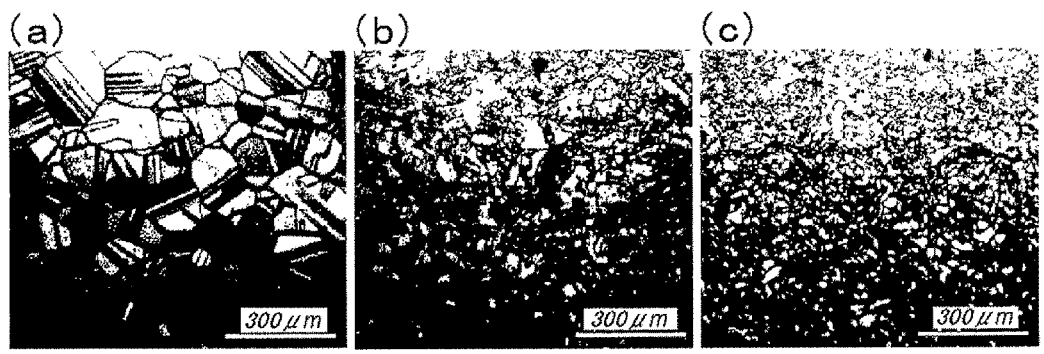
FIG. 6A is an IQ map of an alloy after solution treatment in the method of forming fine grains of a Co—Cr—Mo alloy with nitrogen addition according to an embodiment of the present invention, obtained by an EBSD technique.
FIG. 6B is an IQ map of the alloy after first reverse transformation treatment in the method of forming fine grains of a Co—Cr—Mo alloy with nitrogen addition according to the embodiment, obtained by an EBSD technique.
FIG. 6C is an IQ map of the alloy after second reverse transformation treatment in the method of forming fine grains of a Co—Cr—Mo alloy with nitrogen addition according to the embodiment, obtained by an EBSD technique.

It was confirmed that the crystal grain size of the sample reduced by means of reverse transformation treatment is further reduced by repeating the process surrounded by a broken line shown in FIG. 1 (isothermal aging treatment and reverse transformation treatment) once again. FIGS. 6B and 6C are IQ maps of an alloy after first reverse transformation treatment and second reverse transformation treatment, respectively. As shown in FIGS. 6B and 6C, it was confirmed that the crystal grain diameter was reduced to 15 μm by, for example, subjecting a sample after isothermal aging treatment to first reverse transformation treatment at 1000° C. and quenching to adjust the crystal grain diameter to about 20 μm and further subjecting the resulting sample to isothermal aging treatment again, quenching, and second reverse transformation treatment at 1000° C.

Figure 7:
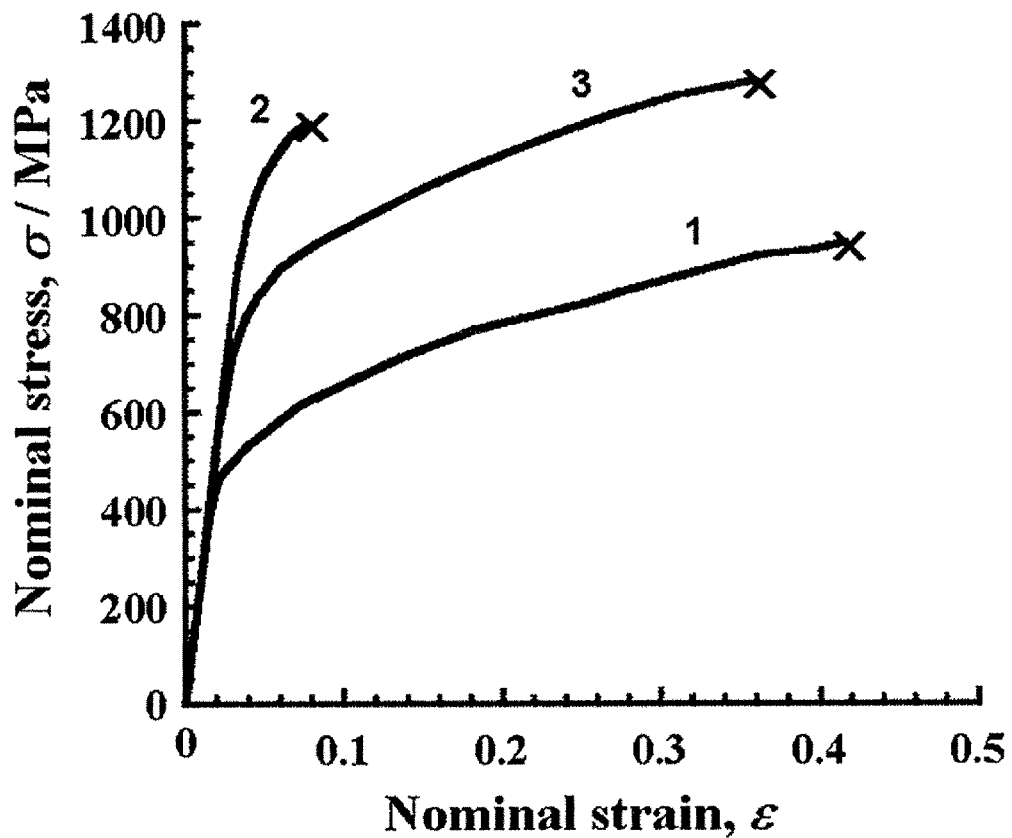
FIG. 7 shows stress-strain curves of a Co—Cr—Mo alloy with nitrogen addition after each heat treatment (1: solution treatment, 2: isothermal aging treatment, 3: reverse transformation treatment) in the method of forming fine grains of a Co—Cr—Mo alloy with nitrogen addition according to an embodiment of the present invention.

FIG. 7 is a graph showing stress-strain curves of a Co—Cr—Mo alloy with nitrogen addition after each heat treatment. In FIG. 7, "1" shows a sample after solution treatment, "2" shows a sample after isothermal aging treatment, and "3" shows a sample after reverse transformation treatment. As shown in FIG. 7, it can be confirmed that the sample subjected to reverse transformation treatment has excellent mechanical properties such as high toughness and high strength with good ductility, compared to the samples subjected to solution treatment or isothermal aging treatment.

The alloys subjected to each heat treatment were subjected to a tensile test. Table 2 shows the 0.2% proof stress, the ultimate tensile strength (UTS), and the fracture elongation obtained by the tensile test. As references, values of hot working finish and annealing finish, which are shown in JIS T 7402-2, a standard of Co—Cr—Mo casting alloy for surgical implant applications, are also shown. As shown in Table 2, it was confirmed that the tensile properties of an alloy subjected to reverse transformation treatment were equivalent or superior to those of hot working finish and annealing finish of JIS T 7402-2 standard.

TABLE 2

| Treatment | Solution treatment | Aging treatment | Reverse transformation treatment | JIS T 7402-2 Annealing | JIS T 7402-2 Hot working |
|---|---|---|---|---|---|
| 0.2% Proof stress (MPa) | 450 | 920 | 690 | >550 | >700 |
| UTS (MPa) | 908 | 1179 | 1282 | >750 | >1000 |
| Fracture elongation | 0.41 | 0.08 | 0.33 | >0.16 | >0.12 |

Example 2

1. Experimental Method

A Co—Cr—Mo alloy with nitrogen addition having a sample alloy composition composed of 29% by weight of Cr, 6.0% by weight of Mo, 0.02% by weight of C, 0.13% by weight of N, and 64.85% by weight of Co was made into a powder by gas atomizing. This powder was sintered at 1060° C. for 2 hours to obtain a sintered compact having a single γ-phase. The sintered compact subjected to solution treatment was, as a starting sample, subjected to isothermal aging treatment and then reverse transformation treatment as in Example 1.

2. Experimental Results

Figure 8:
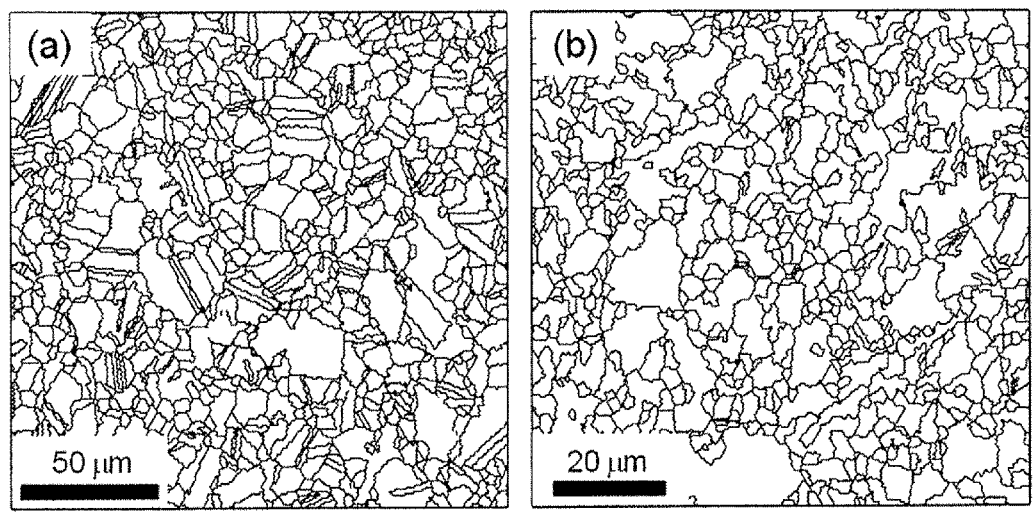
FIG. 8A shows boundaries of crystal grains (boundary map) of an initial microstructure of a sintered compact after solution treatment in the method of forming fine grains of a Co—Cr—Mo alloy with nitrogen addition according to an embodiment of the present invention, obtained by an EBSD technique.
FIG. 8B shows boundaries of crystal grains (boundary map) of a structure after reverse transformation treatment in the method of forming fine grains of a Co—Cr—Mo alloy with nitrogen addition according to the embodiment, obtained by an EBSD technique.

The sintered compact was subjected to isothermal aging treatment and then water quenching to form a multi-phase structure composed of an ε-phase and a Cr nitride. Subsequently, the sintered compact was subjected to reverse transformation treatment and then water quenching. FIGS. 8A and 8B show boundaries of crystal grains (boundary map) of the initial structure and the structure after reverse transformation treatment, respectively, obtained by an EBSD technique. As shown in FIGS. 8A and 8B, it can be confirmed that the structure subjected to reverse transformation treatment has a crystal grain structure finer than that of the initial structure of the starting sample.

Example 3

1. Experimental Method

A commercially available metal injection molding (MIM) material having a nominal composition composed of 29% by weight of Cr, 6.0% by weight of Mo, 0.02% by weight of C, 0.30% by weight of N, and 64.68% by weight of Co was, as a starting sample, subjected to isothermal aging treatment and then reverse transformation treatment as in Example 1.

2. Experimental Results

Figure 9:
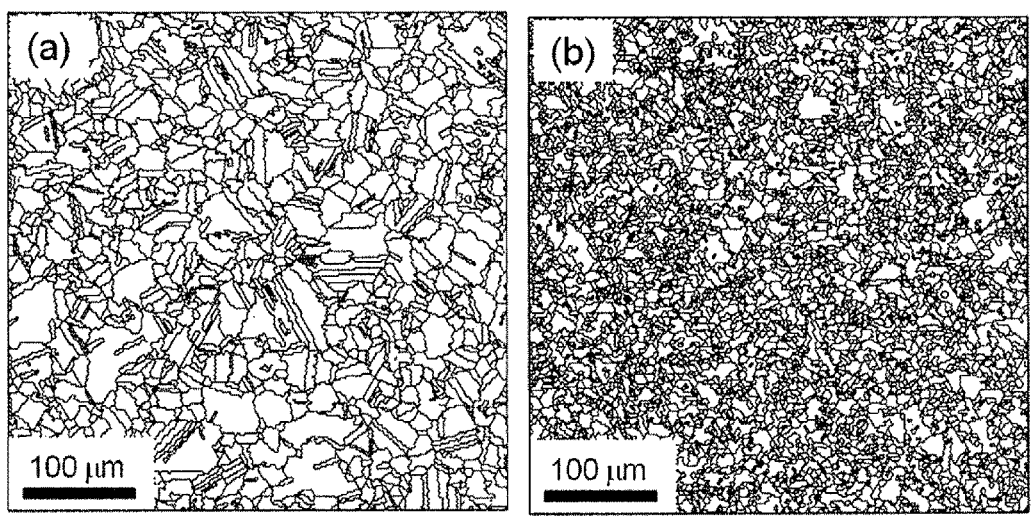
FIG. 9A shows boundaries of crystal grains (boundary map) of an initial microstructure of an MIM material in the method of forming fine grains of a Co—Cr—Mo alloy with nitrogen addition according to an embodiment of the present invention, obtained by an EBSD technique.
FIG. 9B shows boundaries of crystal grains (boundary map) of a structure after reverse transformation treatment in the method of forming fine grains of a Co—Cr—Mo alloy with nitrogen addition according to the embodiment, obtained by an EBSD technique.
Figure 10:
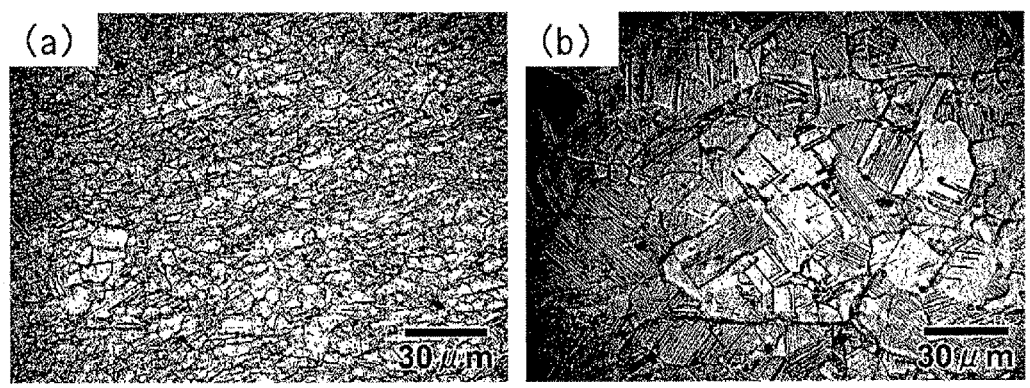
FIG. 10A is an optical micrograph of a cross section near the surface of a round bar material (φ 15) produced by hot swage treatment.
FIG. 10B is an optical micrograph of the cross section at a central portion of the round bar material (φ 15) produced by hot swage treatment.

The starting sample was subjected to isothermal aging treatment and then water quenching to form a multi-phase structure composed of an ε-phase and a Cr nitride. Subsequently, the sample was subjected to reverse transformation treatment and then water quenching. FIGS. 9A and 9B show boundaries of crystal grains (boundary map) of the initial structure and the structure after reverse transformation treatment, respectively, obtained by an EBSD technique. As shown in FIGS. 9A and 9B, it can be confirmed that the structure subjected to reverse transformation treatment has a structure composed of crystal grains that are more uniform and finer than those of the MIM material having the initial microstructure.

As shown in Examples 1 to 3, the method of forming fine grains of a Co—Cr—Mo alloy with nitrogen addition according to the embodiment of the present invention can easily obtain a uniform fine grain structure only by heat treatment utilizing reverse transformation, without performing thermomechanical treatment, unlike a method forming fine grains by hot forging utilizing recrystallization. The mechanical reliability of the Co—Cr—Mo alloy with nitrogen addition can be improved by this formation of fine grains. In addition, since the formation can be performed only by heat treatment, a uniform fine grain structure can be obtained even if a person who conducts the formation does not have a high degree of specialization.

In the method of forming fine grains of a Co—Cr—Mo alloy with nitrogen addition according to the embodiment of the present invention, since thermomechanical treatment is not performed, the material to be used may have any shape and size, and even a compact material, a material having a complex shape, or a commercially available product can be formed into fine grains. In addition, since the method does not need a large-sized forging apparatus and does not require a person who conducts the method to have a forging skill, the method is excellent in universal use. The method of forming fine grains of a Co—Cr—Mo alloy with nitrogen addition according to the embodiment of the present invention can be applied to any Co—Cr—Mo alloy with nitrogen addition that forms a multi-phase structure composed of an ε-phase and a Cr nitride by isothermal aging treatment, whatever the process of producing the alloy. Thus, the method can be widely applied.

The invention claimed is:

1. A method of forming fine grains of a Co—Cr—Mo alloy with nitrogen addition, comprising:
   subjecting a Co—Cr—Mo alloy with nitrogen addition composed of 26 to 35% by weight of Cr, 2 to 8% by weight of Mo, 0.1 to 0.3% by weight of N, and balance of Co to a solution treatment;

subjecting the alloy to an isothermal aging treatment by holding the alloy at 670 to 830° C. for a predetermined period of time to form a multi-phase structure composed of an s-phase and a Cr nitride by means of the isothermal aging treatment;

cooling the alloy; and subjecting the alloy to a reverse transformation treatment in which the alloy is heated at a temperature range of 870 to 1100° C. for reverse transformation to a single γ-phase from the multi-phase structure composed of an s-phase and a Cr nitride.

2. The method of forming fine grains of a Co—Cr—Mo alloy with nitrogen addition according to claim 1, wherein the Co—Cr—Mo alloy with nitrogen addition to be subjected to the solution treatment contains 0.2% by weight or less of Ni.

3. The method of forming fine grains of a Co—Cr—Mo alloy with nitrogen addition according to claim 1, wherein the Co—Cr—Mo alloy with nitrogen addition to be subjected to the solution treatment contains 0.35% by weight or less of C.

4. The method of forming fine grains of a Co—Cr—Mo alloy with nitrogen addition according to claim 1, wherein the holding time of the isothermal aging treatment is 63000 seconds or more.

5. The method of forming fine grains of a Co—Cr—Mo alloy with nitrogen addition according to claim 1, wherein the reverse transformation treatment is performed at a temperature range of 920 to 1000° C. for 300 seconds or more.

6. The method of forming fine grains of a Co—Cr—Mo alloy with nitrogen addition according to claim 1, wherein the reverse transformation treatment is performed at a temperature range of 1000 to 1100° C. for 50 seconds or more.

7. The method of forming fine grains of a Co—Cr—Mo alloy with nitrogen addition according to claim 1, further comprising:

cooling the alloy after the reverse transformation treatment: and repeating the isothermal aging treatment and the reverse transformation treatment.

\* \* \* \* \*